US00PP33867P2

(12) United States Plant Patent
Ullrich

(10) Patent No.: US PP33,867 P2
(45) Date of Patent: Jan. 18, 2022

(54) ***ROSA* PLANT NAMED 'ESM R394'**

(50) Latin Name: *Rosa hybrida*
Varietal Denomination: ESM R394

(71) Applicant: Clarisse Ullrich, Quito (EC)

(72) Inventor: Clarisse Ullrich, Quito (EC)

(73) Assignee: TECNOVIV LLC, Miami, FL (US)

( * ) Notice: Subject to any disclaimer, the term of this patent is extended or adjusted under 35 U.S.C. 154(b) by 0 days.

(21) Appl. No.: 16/945,792

(22) Filed: Jul. 31, 2020

(51) Int. Cl.
*A01H 5/02* (2018.01)
*A01H 6/74* (2018.01)

(52) U.S. Cl.
USPC ..... Plt./138
CPC ..... *A01H 6/749* (2018.05); *A01H 5/02* (2013.01)

(58) Field of Classification Search
USPC ..... Plt./140, 108, 138, 139
CPC ..... A01H 5/0222
See application file for complete search history.

(56) References Cited

PUBLICATIONS

Plant U.S. Appl. No. 16/945,786; Clarisse Ullrich; filed Jul. 31, 2020; 22 pages.*

* cited by examiner

*Primary Examiner* — Kent L Bell
(74) *Attorney, Agent, or Firm* — C. Anne Whealy

(57) ABSTRACT

A new and distinct cultivar of Rose plant named 'ESM R394', characterized by its upright and strong flowering stems; moderately vigorous to vigorous growth habit; dark green-colored leaves; purplish pink-colored flowers; and excellent postproduction longevity.

1 Drawing Sheet

Botanical designation: *Rosa hybrida.*
Cultivar denomination: 'ESM R394'.

CROSS-REFERENCED TO CLOSELY-RELATED APPLICATIONS & STATEMENT REGARDING PRIOR DISCLOSURES BY INVENTOR/APPLICANT AND ASSIGNEE

U.S. Plant Patent application:
Title: *Rosa* Plant Named 'ESM R325'
Inventor/Applicant: Clarisse Ullrich
Filed: Jul. 31, 2020
Ser. No. 16/945,786
European Community Plant Breeders' Rights application:
Filed: Jun. 27, 2019
Application number: 2019/1594
Ecuadorian Plant Breeders' Rights application:
Filed: May 9, 2019
Application number: 1589-19

There have been no offers for sale anywhere in the world prior to the effective filing date of this Application and no accessibility to one of ordinary skill in the art could have been derived from the printed Plant Breeder's Rights documents.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exception under 35 U.S.C. 102(b)(1) for disclosure and/or sales prior to the filing date but less than one year prior to the effective filing date.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R394'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in March, 2014 of a proprietary Rose selection identified as Line R567, not patented, as the female, or seed, parent with a proprietary Rose selection identified as Line R770, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in July, 2015.

Asexual reproduction of the new Rose plant by bud grafting in El Quinche, Pichincha, Ecuador since August, 2015 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R394'. These characteristics in combination distinguish 'ESM R394' as a new and distinct Rose plant:

1. Upright and strong flowering stems.
2. Moderately vigorous to vigorous growth habit.
3. Dark green-colored leaves.
4. Purplish pink-colored flowers.
5. Excellent postproduction longevity.

Plants of the new Rose differ from plants of the female parent selection in the following characteristics:

1. Plants of the new Rose are more vigorous than plants of the female parent selection.
2. Stems of plants of the new Rose are shorter than stems of plants of the female parent selection.
3. Flowers of plants of the new Rose have fewer petals than flowers of plants of the female parent selection.
4. Flowers of plants of the new Rose are purplish pink in color whereas flowers of plants of the female parent selection are red in color Plants of the new Rose differ from plants of the male parent selection in the following characteristics:

1. Plants of the new Rose are not as vigorous as plants of the male parent selection.
2. Flowers of plants of the new Rose have fewer petals than flowers of plants of the male parent selection.
3. Flowers of plants of the new Rose are purplish pink in color whereas flowers of plants of the male parent selection are dark red in color.

Plants of the new Rose can be compared to plants of *Rosa hybrida* 'ESM R325', disclosed in U.S. Plant Pat. No. 33,327. Plants of the new Rose differ from plants of 'ESM R325' in the following characteristics:

1. Plants of the new Rose flower about eleven days earlier than plants of 'ESM R325'.
2. Plants of the new Rose have larger flowers with fewer petals than plants of 'ESM R325'.
3. Plants of the new Rose have purplish pink-colored flowers whereas plants of 'ESM R325' have red-colored flowers.

Plants of the new Rose can also be compared to plants of *Rosa hybrida* 'ESM R044', disclosed in U.S. Plant Pat. No. 24,403.

Plants of the new Rose differ from plants of 'ESM R044' in the following characteristics:

1. Plants of the new Rose are taller than plants of 'ESM R044'.
2. Plants of the new Rose have slightly larger flowers than plants of 'ESM R044'.
3. Flowers of plants of the new Rose have fewer petals than flowers of plants of 'ESM R044'.

BRIEF DESCRIPTION OF THE PHOTOGRAPH

The accompanying colored photograph illustrates the overall appearance of the new Rose plant showing the colors as true as it is reasonably possible to obtain in colored reproductions of this type. Colors in the photograph may differ slightly from the color values cited in the detailed botanical description which accurately describe the colors of the new Rose plant.

On the left side of the sheet is a side perspective of a typical flowering stem of 'ESM R394'.

On the upper right side of the sheet is a close-up view of a typical developed flower of 'ESM R394'.

On the center and lower right side of the sheet are close-up views of the upper and lower surfaces of typical leaves of 'ESM R394'.

DETAILED BOTANICAL DESCRIPTION

The aforementioned photograph, following observations and measurements describe plants grown in 10-liter containers in a polyethylene-covered greenhouse in El Quinche, Pichincha, Ecuador and under typical hydroponic Rose production practices. Plants were pinched 14 weeks after planting and were 106 weeks old when the photograph was taken and 46 weeks old when the description was taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2015 Edition, except where general terms of ordinary dictionary significance are used.

Botanical classification: *Rosa hybrida* 'ESM R394'.

Parentage:

*Female, or seed, parent*.—Proprietary seedling selection of *Rosa hybrida* identified Line R567, not patented.

*Male, or pollen, parent*.—Proprietary seedling selection of *Rosa hybrida* identified Line R770, not patented.

Propagation:

*Type*.—By bud grafting.

*Time to initiate roots, summer*.—About 15 days at temperatures about 26° C. to 30° C.

*Time to produce a rooted young plant, summer*.—About 30 days at temperatures about 22° C. to 26° C.

*Root description*.—Medium in thickness, fibrous; typically greyish brown in color, actual color of the roots is dependent on substrate composition, water quality, fertilizers, substrate temperature and age of roots.

*Rooting habit*.—Moderately freely branching; dense.

Plant description:

*Plant and growth habit*.—Perennial shrub; upright and strong flowering stems; typically grown as a standard type; moderately vigorous to vigorous growth habit and rapid growth rate.

*Productivity*.—Plants of the new Rose are highly productive with more than ten flowering stems developing per plant per year.

*Plant height*.—About 195 cm.

*Plant width* (*spread*).—About 54 cm.

*Lateral branches*.—Length: About 92 cm. Diameter: About 7.8 mm. Internode length: About 5.2 cm. Texture and luster: Smooth, glabrous; matte. Strength: Strong. Color, developing: Close to 146A. Color, developed: Close to 144A; at the internodes, close to N146A and N199A. Thorns: Number per linear cm: About one to two. Shape: Triangular with sharp acuminate apices; slightly incurved. Height: About 8.5 mm. Length, at base: About 1 cm. Color, immature: Close to 181B. Color, mature: Close to 179B.

Leaf description:

*Arrangement*.—Alternate; compound with typically five to seven leaflets per leaf.

*Leaf length*.—About 19.4 cm.

*Leaf width*.—About 13.9 cm.

*Leaflet length*.—About 8.2 cm.
*Leaflet width*.—About 4.8 cm.
*Leaflet shape*.—Ovate.
*Leaflet apex*.—Acuminate.
*Leaflet base*.—Obtuse.
*Leaflet margin*.—Serrate.
*Leaflet texture and luster, upper surface*.—Smooth, glabrous; moderately glossy.
*Leaflet texture and luster, lower surface*.—Smooth, glabrous; matte.
*Leaflet venation pattern*.—Pinnate.
*Leaflet color*.—Developing leaflets, upper surface: Close to NN137A. Developing leaflets, lower surface: Close to 147B. Fully expanded leaflets, upper surface: Close to NN137A; venation, close to 151B. Fully expanded leaflets, lower surface: Close to 147A; venation, close to 145B.
*Petioles*.—Length: About 1.9 cm. Diameter: About 2.2 mm. Strength: Strong. Texture and luster, upper surface: Prickly; matte. Texture and luster, lower surface: Smooth, glabrous; moderately glossy. Color, upper surface: Close to between 179A and 166A. Color, lower surface: Close to 146A.
*Stipules*.—Arrangement and appearance: Two, adnate to the petiole, leafy in appearance. Length: About 2.7 cm. Width: About 1.9 mm. Shape: Roughly deltoid. Apex: Acuminate, tapered. Base: Tapered. Margin: Irregular. Texture and luster, upper and lower surfaces: Smooth, margins, pubescent; membranous; matte. Venation pattern: Pinnate. Color, upper surface: Close to NN137A. Color, lower surface: Close to 147A.

Flower description:
*Flower type and arrangement*.—Symmetrical rosette flowers; flowers typically grown as a standard type with one terminal flower per flowering stem; flowers face upright.
*Flowering season*.—Plants of the new Rose flower year-round under greenhouse conditions; early flowering habit, plants begin flowering about 80 days after pinching.
*Flower diameter*.—About 13.8 cm.
*Flower depth* (*height*).—About 6.4 cm.
*Flower longevity*.—Excellent postproduction longevity; flowers maintain good substance for about 18 to 20 days on the plant and for about 14 to 16 days as a cut flower; flowers persistent.
*Fragrance*.—None detected.
*Flower buds*.—Length: About 5.9 cm. Diameter: About 5.3 cm. Shape: Ovoid. Texture and luster: Smooth, glabrous; matte. Color: Close to N186C and 146A.
*Petals*.—Quantity: About 27 per flower; petals imbricate. Length: About 7.1 cm. Width: About 7.9 cm. Shape: Obovate. Apex: Short acute. Base: Obtuse. Margin: Entire; moderately undulate. Texture and luster, upper and lower surfaces: Smooth, glabrous; papery to coriaceous; matte. Color: When opening, upper surface: Close to N66A. When opening, lower surface: Close to N66B. Fully opened, upper surface: Close to N66B; venation, close to N66B; color becoming closer to N57A with development. Fully opened, lower surface: Close to N66B; towards the base, close to N57B; color becoming closer to N57B with development.
*Petaloids*.—Quantity: About four in a single whorl. Length: About 4.6 cm. Width: About 3.1 cm. Shape: Irregularly shaped. Apex: Variable. Base: Tapered. Margin: Irregular; undulate. Texture and luster, upper surface: Somewhat rugose, glabrous; papery to coriaceous; matte. Texture and luster, upper surface: Smooth, glabrous; papery to coriaceous; moderately glossy. Color: When opening, upper surface: Close to N57A. When opening, lower surface: Close to N57B. Fully opened, upper surface: Close to N57B; venation, close to N57D; color becoming closer to between N57A and N66B and proximally, close to 155C with development. Fully opened, lower surface: Close to N57B; venation, close to N57D; color becoming closer to between N57A and N66B and proximally, close to 155B with development.
*Sepals*.—Quantity per flower: Typically five in a single whorl. Length: About 4.4 cm. Width: About 1.6 cm. Shape: Roughly deltoid. Apex: Tapered. Base: Truncate. Margin: Entire; ciliate and/or glandular. Texture and luster, upper surface: Pubescent, leathery; matte. Texture and luster, lower surface: Glabrous, leathery; matte. Color: When opening, upper surface: Close to 144A. When opening, lower surface: Close to 138B. Fully opened, upper surface: Close to 146A. Fully opened, lower surface: Close to 139C.
*Reproductive organs*.—Stamens: Quantity: About 294 per flower. Filament length: About 6.9 mm. Filament color: Close to 54B and 157A. Anther size: About 2.6 mm by 1.9 cm. Anther shape: Reniform. Anther color: Close to 63A and towards the edge, close to 161A. Pollen amount: Moderate. Pollen color: Close to 163A. Pistils: Quantity: About 230 per flower. Pistil length: About 1.8 cm. Stigma diameter: About 1.3 mm. Stigma shape: Broadly reniform. Stigma color: Close to 4C. Style length: About 1.3 cm. Style color: Close to 53B and 157B. Ovary color: Close to 157A. Receptacle height: About 1.2 cm. Receptacle diameter: About 1.6 cm. Receptacle shape: Cup-shaped. Receptacle texture: Smooth, glabrous. Receptacle color: Close to 144A to 144B. Fruits and seeds: To date, fruit and seed development have not been observed on plants of the new Rose.

Pathogen & pest tolerance: Plants of the new Rose have not been observed to be tolerant to pathogens and pests common to Rose plants.

Temperature tolerance: Plants of the new Rose have been observed to tolerate temperatures ranging from 0° C. to 35° C.

It is claimed:

1. A new and distinct Rose plant named 'ESM R394' as illustrated and described.

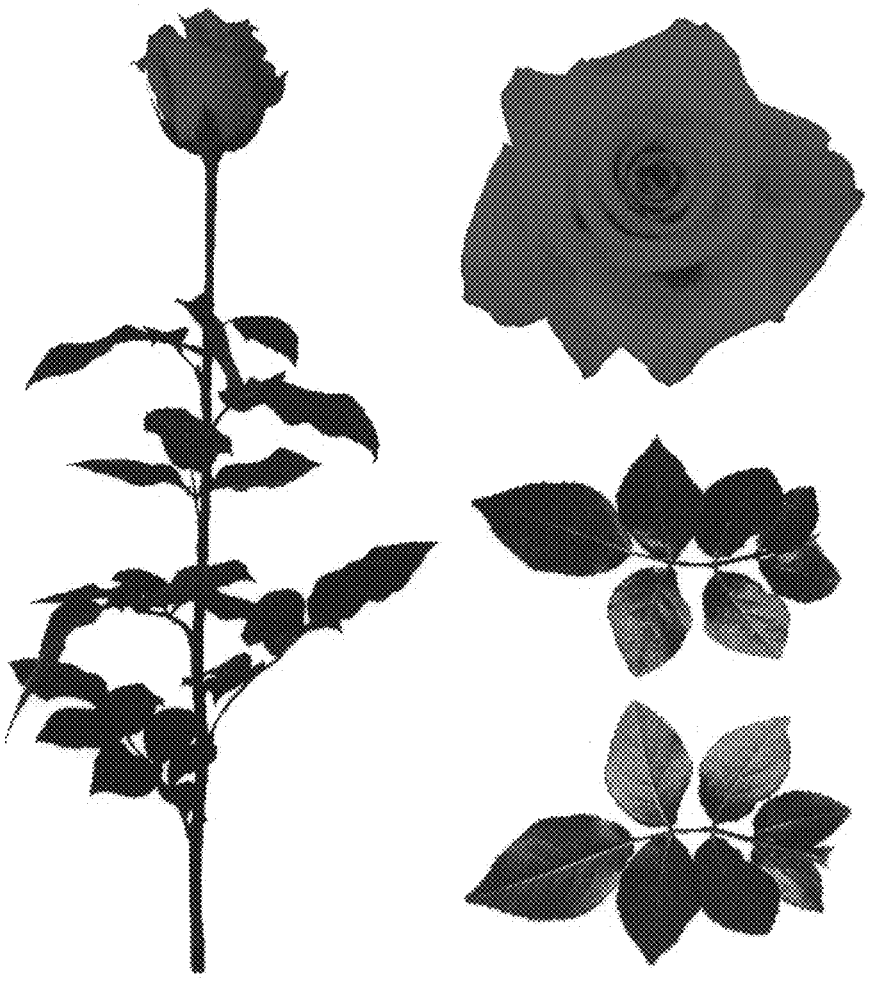

* * * * *